US00PP22244P2

(12) United States Plant Patent
Jones

(10) Patent No.: US PP22,244 P2
(45) Date of Patent: Nov. 15, 2011

(54) APPLE TREE NAMED 'LJ-1000'

(50) Latin Name: ***Malus domestica* Borkh**
Varietal Denomination: LJ-1000

(76) Inventor: Larry D. Jones, Quincy, WA (US)

( * ) Notice: Subject to any disclaimer, the term of this patent is extended or adjusted under 35 U.S.C. 154(b) by 0 days.

(21) Appl. No.: 12/803,821

(22) Filed: Jul. 6, 2010

(51) Int. Cl.
*A01H 5/00* (2006.01)

(52) U.S. Cl. ..... Plt./161

(58) Field of Classification Search ..... Plt./161
See application file for complete search history.

*Primary Examiner* — Annette Para
(74) *Attorney, Agent, or Firm* — Paine Hamblen, LLP

(57) ABSTRACT

A new and distinctive variety of apple tree is described, and which is characterized as to novelty by producing an attractively colored apple which is mature for harvesting and shipment approximately September 16$^{th}$ under the ecological conditions prevailing in Central Washington State.

5 Drawing Sheets

Latin name of the genus and species of the plant claimed: *Malus domestica* Borkh.

BACKGROUND OF THE NEW VARIETY

The present invention relates to a new and distinct variety of apple tree '*Malus Domestica* Borkh', and which has been denominated varietally, hereinafter, as 'LJ-1000', and more particularly to an apple tree which bears an attractive highly colored fruit which is distinguished as to novelty by its firm texture, earlier coloring, and high sugar levels when compared to the closest known variety, and when grown under the ecological conditions prevailing near Quincy, Wash. in the central region of Washington State.

ORIGIN AND ASEXUAL REPRODUCTION

It has long been recognized that an important factor contributing to the success of any new variety of apple tree bearing fruit for the fresh market is its appearance, and respective harvesting date, in relative comparison to other varieties bearing similar fruit in the same season. Similarly, other significant factors affecting the commercial viability of any new strain of apple relates to its flavor, as reflected by its sugar content, as well as the storage characteristics of the fruit.

The new apple tree variety 'LJ-1000' is noteworthy in producing a fruit which is ripe for harvesting and shipment at approximately Sep. 16, 2009 under the ecological conditions prevailing near Quincy, Wash. Further, in contrast to the apple tree which it is most closely similar to, that being, the 'Honeycrisp' apple, U.S. Plant Pat. 7,197, the present tree is distinguished therefrom by developing earlier color which is overall more intense than the fruit produced by the 'Honeycrisp' apple tree (U.S. Plant Pat. 7,197) (See FIG. 4). Additionally, the new variety shows greatly enhanced storage characteristics in relative comparison to the fruit produced by the 'Honeycrisp' apple tree (U.S. Plant Pat. 7,197) when grown under similar ecological conditions.

The new variety of apple tree as described herein was discovered within the cultivated region of an apple orchard, owned by the inventor, and which is located near Quincy, Wash. in 2005. In this regard, the present variety was discovered following the grafting of 'Honeycrisp' apple tree (U.S. Plant Pat. No. 7,197) wood onto then existing Sansa apple trees (U.S. Plant Pat. No. 6,519) during the 2003 growing season. This grafting took place within the same orchard. During routine orchard operation in 2005, it was discovered that one of these grafted trees (the present variety) colored earlier and to a greater extent than the adjacent 'Honeycrisp' apple tree (U.S. Plant Pat. No. 7,197). In 2006, scion wood was removed from this earlier discovered tree, and then grafted onto other Sansa apple trees (U.S. Plant Pat. No. 6,519) growing in this same orchard. These second generation test trees have been continually observed until most recently. Also, during this time period, the inventor diligently compared and contrasted the first asexually reproduced trees, and the fruit produced thereby with that of the originally discovered tree. In all respects, they appeared to be identical. None of the foregoing test trees have ever been sold or offered for sale to the public while undergoing this comparative testing and evaluation.

It has been confirmed through all the aforementioned observations that the earlier asexual reproductions, as noted above, resulted in apple trees which produce fruit which possess the same distinctive characteristics as the original newly discovered tree.

SUMMARY OF THE VARIETY

The 'LJ-1000' apple tree is characterized principally as to novelty by producing an attractively colored fruit which is ripe for harvesting and shipping approximately September 16 under the ecological conditions prevailing in central Washington State. In contrast to the variety which it is most closely similar to, that being, the 'Honeycrisp' (U.S. Plant Pat. No. 7,197), which matures at about the same time at this geographical location, it is distinguishable therefrom by being more highly colored at harvest and having improved storage characteristics. In addition to the foregoing, the 'LJ-1000' apple tree has noticeably elevated sugar levels which clearly distinguishes it from other varieties which it is most closely similar to such as the 'Honeycrisp' apple tree (U.S. Plant Pat. No. 7,197). These and other characteristics make the present apple tree variety highly desirable as a producer of fresh fruit for both local and long distance markets.

Figure 1:
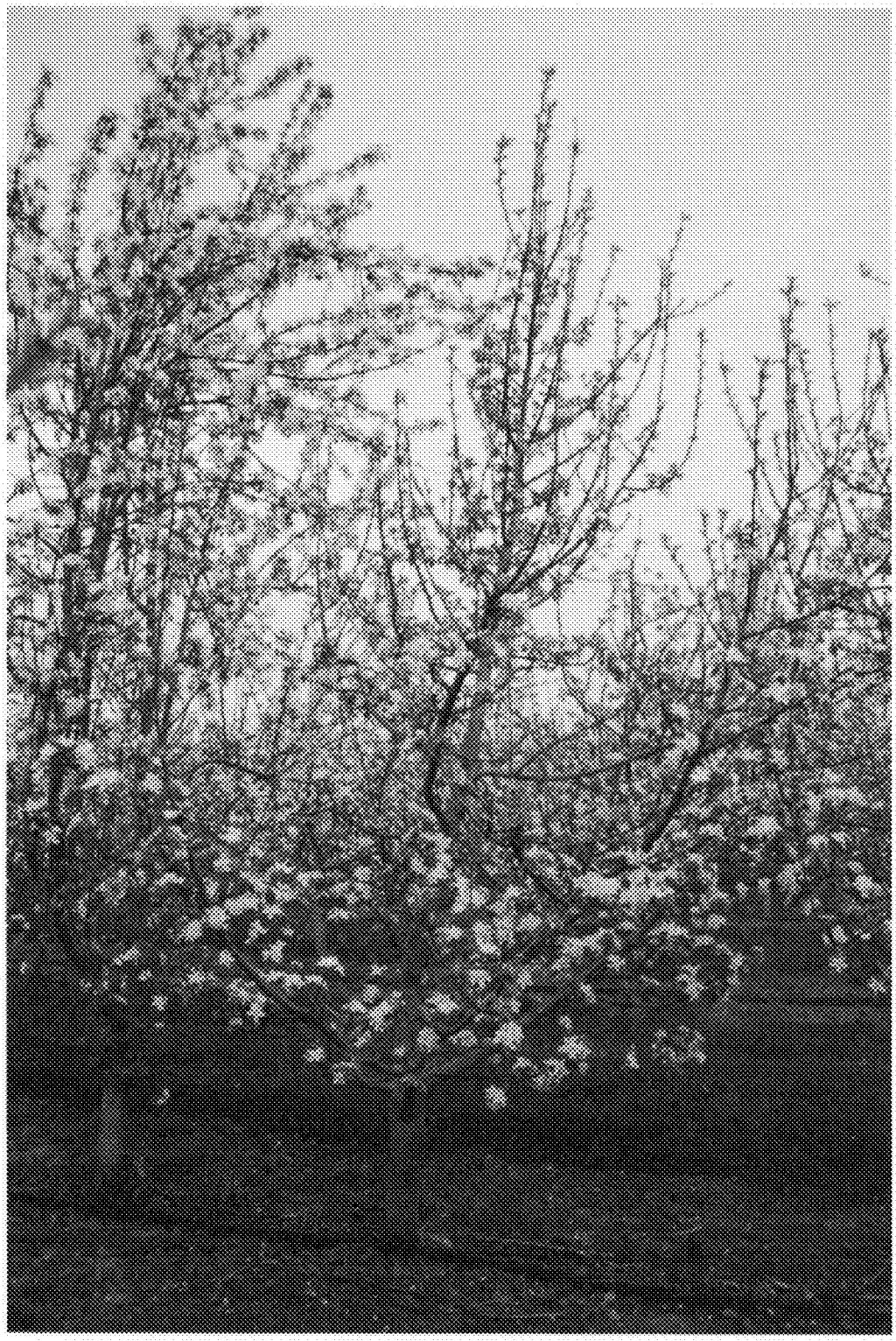
FIG. 1 is a picture of the present variety of apple tree growing under typical conditions in an orchard in central Washington State.
Figure 2:
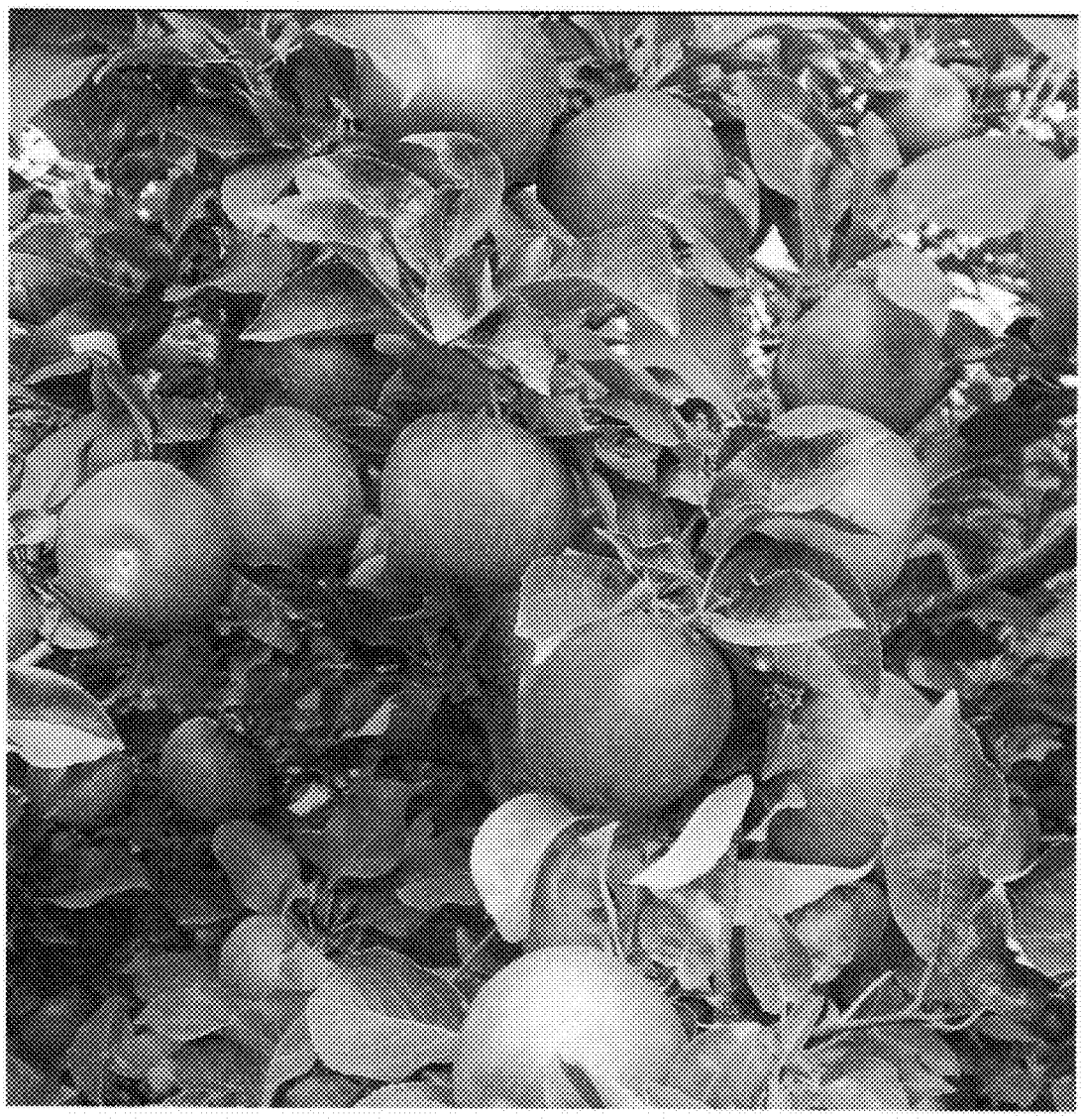
FIG. 2 is a picture of a 'Honeycrisp' apple tree (U.S. Plant Pat. No. 7,197) growing under typical conditions in an orchard in central Washington State.
Figure 3:
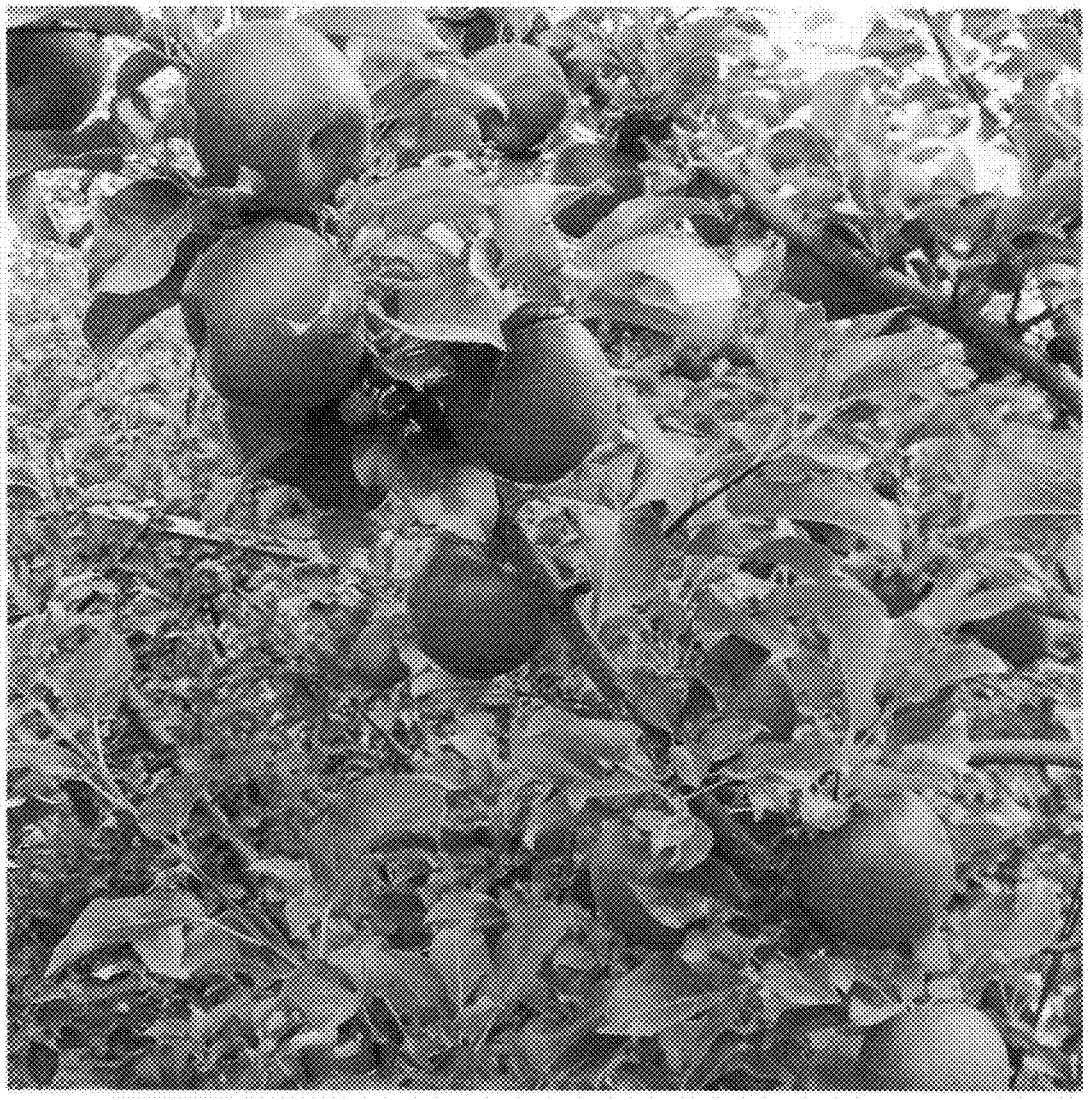
FIG. 3 is a picture of the present variety of apple tree. The picture of FIG. 3 was taken on the same day as the picture of FIG. 2 and when considered along with the picture of FIG. 2 illustrates the early coloring of the fruit of the present variety relative to the fruit of the 'Honeycrisp' apple tree (U.S. Plant Pat. No. 7,197).
Figure 4:
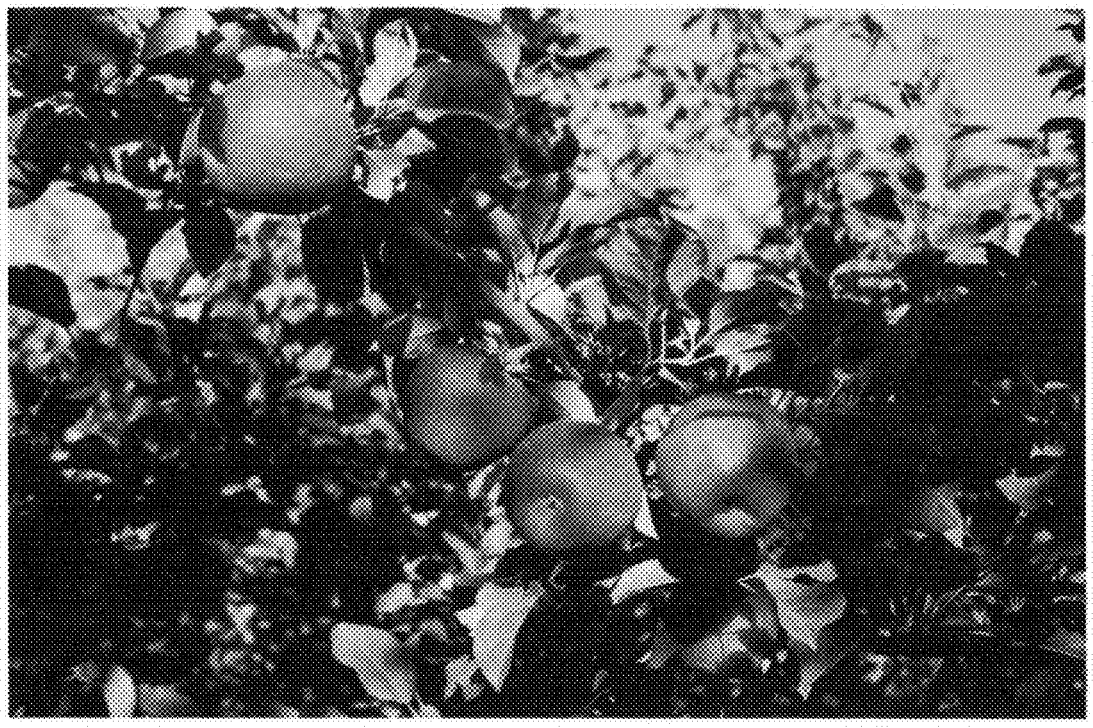
FIG. 4 is a picture of a branch of the present, new variety of apple tree at harvest maturity.
Figure 5:
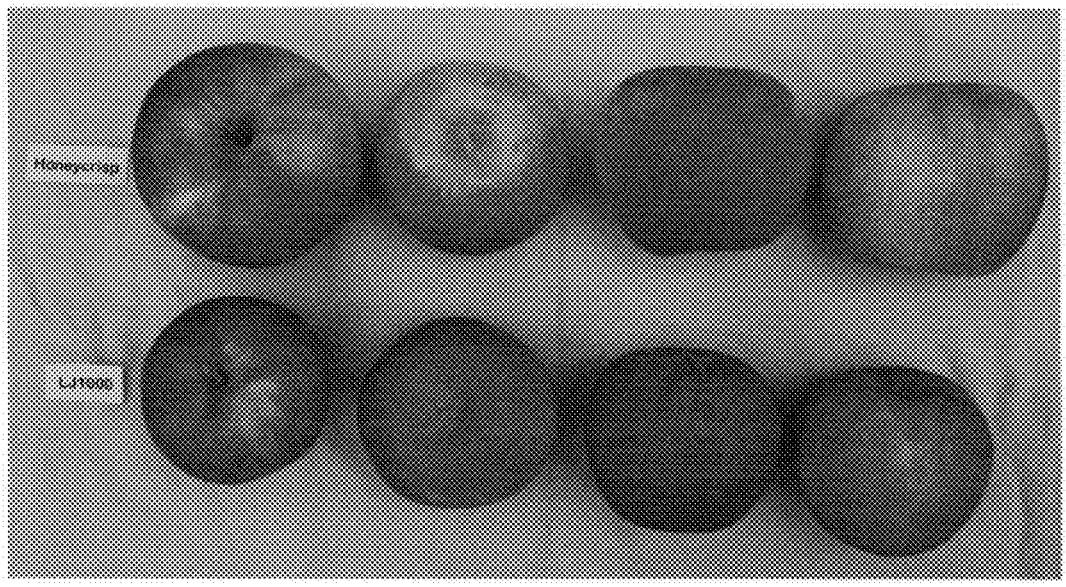
FIG. 5 is a picture which contrasts the fruit of the present variety with that of the fruit produced by the 'Honeycrisp' apple tree (U.S. Plant Pat. No. 7,197) at full maturity and harvest.

The colors in the enclosed photographs are as nearly true as is reasonably possible in color photographs of this type. However, due to chemical development, processing, and printing, the various colors depicted in these photographs may or may not be accurate when compared to the actual botanical specimens. For this reason, future color references should be made to the color plates provided in The Royal Horticulture Society Handbook and descriptions provided hereinafter. Occasionally common color names will also be used.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display the botanical, pomological or other characteristics as set forth, hereinafter. Therefore, this disclosure may not be relied upon to support any future legal claims including, without limitation, any claims relating to the breach of warranty of merchantability, or fitness for any particular purpose, or non-infringement which is directed, in whole, or in part, to the present variety.

DETAILED DESCRIPTION

TREE

Size:
- *Generally.*—The tree as described hereinafter is a second generation asexually reproduced tree which was created in 2005. As a general matter, the present tree is average in size, and pruned so as to benefit a central leader type cultural arrangement.

Vigor: Considered average, although weakly so.
Overall shape: Considered upright and spreading.
Average height: 15 feet.
Average width: 8 feet.
Type: Training of the tree is by means of the central leader type. The tree is a near consistent bearer, and has moderate spur development.
Hardiness: Considered hardy under typical central Washington state ecological conditions.
Productivity: Moderate.

TRUNK

Generally: The trunk has a diameter of about 8.2 cm. when measured about 20 cm. above the surface of the earth on trees that are 5 years old.
Bark texture: Considered smooth.
Bark color: Grey-Brown (RHS N199A).
Lenticels:
- *Generally.*—Present, and moderate in number. The present variety has approximately one lenticel per square centimeter of bark surface area.

Lenticels:
- *Width.*—Approximately 1.5 mm.

Lenticels:
- *Height.*—About 11.4 mm.

Lenticels:
- *Color.*—Orange-White (RHS 159B).

BRANCHES

First year:
- *Branching habit.*—Average first year growth is about 28.5 cm. to about 63 cm. in length.

Branches:
- *Size and texture.*—Considered average for the species.

Diameter: At the mid-point of the branches, the average diameter is about 3.5 to about 5.9 mm.
Bark color:
- *First year branches.*—Grey-Purple group (RHS 183A).

First year branches:
- *Lenticels.*—Considered numerous. Typically about 45 per running cm. of surface area.

Lenticels:
- *Shape.*—Oval.

Internodes:
- *Generally.*—Internodes Distance: About 3.0 to 4.8 cm.

Lenticels:
- *Size.*—About 0.08 mm. long; and about 0.5 mm. wide.

Lenticels:
- *Color.*—White. This color is not distinctive of the variety.

Branch pubescence:
- *First year branches.*—Present and considered light to moderate.

Two year old fruiting branches:
- *Generally.*—Two year old fruiting branches.
- *Diameter.*—When measured at the mid-point of growth, these branches average about 10.8 mm.

Spur development: Generally speaking, the spur development of the present variety is moderate in relative comparison to other common varieties. Spurs range in length from 1 cm. to about 3 cm.
Lenticels:
- *Numbers.*—Numerous, and averaging about 10 lenticels per square centimeters of surface area.

Lenticels:
- *Shape.*—Generally considered round, and about 1-2 mm. in diameter. Occasionally, lenticels appear which have an elongated shape and which are about 0.5 mm. in width, and 1.5 mm. in length.

Scaffold branches:
- *Size.*—Variable from about 3.3 cm., to about 4.6 cm. in diameter, as measured at a distance of about 10 cm. from the trunk.

Scaffold branches:
*Crotch angle.*—The present variety is trained to a central leader formation and the branches typically range from about 60-90 degrees from the vertical.
Scaffold branches:
*Color.*—Grey-Brown (RHS N199A).
Bark lenticels:
*Numbers.*—Numerous, and averaging about 8 per square centimeter of bark surface area.
Lenticels:
*Shape.*—Elongated and averaging about 1 mm. in width and about 4.8 mm. in length.
Lenticels:
*Size.*—Considered small for the species.
Lenticels:
*Color.*—Grey-Yellow (RHS 161D).

LEAVES

Shape: Considered oval. The edges of the leaves tend to fold upwardly.
Texture:
*Upper surface.*—Leathery, smooth and glossy; Lower Surface — soft and velvety.
Leaf color:
*Upper surface.*—Green (RHS 137A).
Leaf color:
*Lower surface.*—Dull green (RHS 148D).
Marginal edge:
*Shape.*—Generally doubly serrate.
Leaf length: About 8.2 cm. to about 10.7 cm.
Leaf width: About 6 cm. to about 6.5 cm.
Leaf tip:
*Shape.*—Mucronate.
Leaf base:
*Shape.*—Rounded.
Mid-vein color:
*Upper surface.*—Green-White. This color is not distinctive of the variety.
Mid-vein:
*Shape.*—Prominent and straight and having white downiness on the lower surface of the leaf.
Mid-vein:
*Width.*—About 0.16 mm.
Petiole:
*Length.*—About 2.6 cm. to about 4.3 cm.
Petiole:
*Diameter.*—About 0.14 mm. to about 0.2 mm.
Petiole:
*Color.*—Yellow-Green (RHS 145C), with highlights of purple (RHS N77B) at the basal end thereof.
Petiole:
*Pubescence.*—Abundant over the length and circumference of the petiole.
Leaf stipules:
*Generally.*—Small and narrow.
Leaf stipules:
*Size.*—About 0.5 cm. to about 1.5 cm. long; and 0.04 cm. to 0.14 cm. wide.
Leaf stipules:
*Color.*—Upper surface, Yellow-Green (RHS 145C); lower surface, (RHS 145D).
Mid vein:
*Generally.*—Considered straight.
Mid-vein pubescence:
*Upper surface.*—Considered light, on the lower surface considered heavy.
Pubescence color: Green-White (RHS 157D).

FLOWERS

Full bloom was observed on Apr. 23, 2010. The average bloom date over the last 5 years was April 20.
Number of blossoms per bud: Variable. From 5-6, typically 6.
Flower size: Considered medium, to medium-large for the species. About 44-55 mm. in diameter.
Petals:
*Width.*—About 15.7 mm.
Petals:
*Length.*—About 22.4 mm.
Petals:
*Color.*—White, and having grey-purple highlights (RHS N66D).
Petal vein color: Reddish-Purple (RHS 67A).
Stamens:
*Numbers.*—About 19-21.
Filiments:
*Length.*—About 3.1-7.8 mm.
Filiments:
*Color.*—Grey-Yellow (RHS 160D).
Anthers:
*Shape.*—Kidney shaped.
Anthers:
*Width.*—About 1.5 mm.
Anthers:
*Length.*—About 1.8 mm.
Anthers:
*Color.*—The color at maturity is yellow-white (RHS 158D).
Pistil:
*Length.*—About 11.8-12.7 mm.
Styles:
*Numbers.*—5.
Styles:
*Form.*—Fused near the base, and having a white pubescent color at the union.
Styles:
*Average length.*—About 9.5 mm.
Styles:
*Color.*—Typically yellow-green (RHS 149D).
Stigma:
*Shape.*—Club shaped.
Stigma:
*Color.*—Grey-Yellow (RHS 162A).
Sepals:
*Numbers.*—5 per blossom.
Sepals:
*Shape.*—Generally curled back toward the peduncle. The overall shape is considered deltoid, and the tip being acuminate. The base is truncated in shape.
Sepals:
*Length.*—About 7.4 mm.
Sepals:
*Width.*—About 4 mm.
Sepals:
*Color.*—The sepals have an abundant white pubescence which is present on both the upper and lower surfaces. The sepal color is green (RHS 143C). The tips of the sepals are highlighted and appear grey-purple (RHS 186A).

Peduncle:
*Length.*—Variable from about 15.4 to about 23.8 mm.
Peduncle:
*Color.*—Green (RHS 138B).
Peduncle:
*Pubescence.*—Considerable white downiness is present over the entire surface.

FRUIT

Fruit:
*Maturity when described.*—The present fruit is described at full commercial maturity. These measurements were taken from first generation trees presently growing in the test orchard which is located near Quincy, Wash.
Fruit form: Considered round. As a general matter, the equatorial diameter cross-section is irregular.
Size: Considered average for the species when measured under the typical crop loads. Average equatorial diameter is about 8.39 cm.
Average axial diameter: About 7.12 cm.
Date of harvesting: Sep. 16, 2009 under the typical ecological conditions prevailing in central Washington State. In comparison to the 'Honeycrisp' apple trees grown at approximately the same geographical location, the 'Honeycrisp' apple trees (U.S. Plant Pat. No. 7,197) matures at approximately the same time in the orchard of origin.
Stem:
*Length.*—Considered average in length and diameter. The average length is about 1.9 mm.; and the average diameter is about 2.5 mm.
Stem cavity:
*Average width.*—About 3.76 mm.
Stem cavity:
*Average depth.*—About 1.81 cm.
Stem cavity:
*Shape.*—Acute.
Stem cavity:
*Shape.*—Acute. No lipping is apparent.
Basin cavity:
*Average width.*—About 3.42 cm.
Basin cavity:
*Average depth.*—11.24 mm.
Basin cavity:
*Surface texture.*—Lightly puckered around the eye and having a downy pubescent base. Only slight ribbing is evident.
Eye:
*Shape.*—Erect and having somewhat reflexed tips.
Sepals:
*Surface texture.*—Downy.
Fruit skin:
*Generally.*—Glabrous and a bloom is present at harvest.
Overall appearance:
*Generally.*—The fruit surface is covered with a blush and has a mottled appearance where the fruit has been shaded.
Skin color:
*Overcolor.*—Red (RHS 46A).
Skin color:
*Undercolor.*—Orange-Red (RHS 34D).
Skin lenticels:
*Generally.*—Present, distinct and appearing more numerous towards the calyx end of the fruit.
Lenticels:
*Numbers.*—About 4 per square centimeter typically appear at the stem end of the fruit, and about 10 per square centimeter generally appear in the region of at the equatorial axis. Still further, 24 lenticels typically appear per square centimeter at the calyx end of the fruit.
Lenticels:
*Surface texture.*—Smooth relative to the skin.
Lenticels:
*Color.*—White. This color is not distinctive of the variety.
Lenticels:
*Size.*—Variable from 0.1 to 0.8 mm. in diameter.
Core:
*Generally.*—Average in size.
Core position: Considered medium.
Core line position: Basal clasping.
Cell shape: Elliptical.
Tube:
*Shape.*—Cone shaped.
Stamen position:
*Generally.*—Considered median.
Axis position: Considered axial and closed.
Seed number: Generally 2 occasionally 1.
Seed:
*Shape.*—Acuminate.
Seed:
*Length.*—About 8.5 mm.
Seed:
*Width.*—About 4.4 mm.
Seed:
*Color.*—Grey-Orange (RHS 166A).
Fruit flesh:
*Generally.*—Considered firm, crisp and juicy.
Flesh color: White (RHS 2B).
Fruit aroma: Considered mild and typical for the species.
Starch: Generally about 5.03.
Fruit pressure: 13.98.
Soluable solids: 11.8. In comparison to the fruit produced by the 'Honeycrisp' apple tree at the same geographical location, and at various dates, these values are:

| Date | Apple | Ave. Pressure | Ave. Sugar | Ave. Starch |
|---|---|---|---|---|
| Sep. 16, 2009 | Honeycrisp | 13.98 | 11.8 | 5.03 |
| Sep. 16, 2009 | LJ1000 | 14.39 | 12.8 | 5.03 |
| Mar. 17, 2010 | Honeycrisp | 13.96 | 13.0 | 6.0 |
| Mar. 17, 2010 | LJ1000 | 15.77 | 13.0 | 6.0 |

Keeping quality: Considered excellent for the species. The present variety has been kept up to six months in common storage with no deleterious effects noted. Still further, the fruit flesh resists turning to a brown color after being exposed to the ambient atmosphere.
Pollination:
*Generally.*—Any diploid apple maturing in the same blooming season may pollinate this tree.
Fruit use: Considered a fresh dessert apple for both local and long distance markets.

Disease and insect resistance: No unusual susceptibilities to insect diseases found in the region of Central Washington were noted. The present variety has not been subjected to either drought or other adverse environmental conditions to determine its suitability for those conditions.

Although the new variety of apple tree herein denominated as 'LJ-1000' possesses the characteristics when grown under the ecological conditions prevailing near Quincy, Wash. It is to be understood variations of the usual magnitude and characteristics incident to changes in growing conditions, fertilizing, pruning and pest control are to be expected.

Having thus described and illustrated my new variety of apple tree, what I claim is new, and desire to secure by Plant Letters Patent is:

1. A new and distinct variety of apple tree as substantially illustrated and described, and which is characterized principally to novelty by producing an attractively colored apple which is mature for harvesting and shipment on approximately September 16th under the ecological conditions prevailing near Quincy, Wash.

* * * * *

UNITED STATES PATENT AND TRADEMARK OFFICE

CERTIFICATE OF CORRECTION

PATENT NO. : PP22,244 P2
APPLICATION NO. : 12/803821
DATED : November 15, 2011
INVENTOR(S) : Larry D. Jones It is certified that error appears in the above-identified patent and that said Letters Patent is hereby corrected as shown below:

In the Specification

Column 1, line 40, replace the text beginning "The new variety of apple tree" and ending "in this same orchard." in column 2, line 11, with the following text:

The new variety of apple tree as described herein was discovered within the cultivated region of an apple orchard, owned by the inventor, and which is located near Quincy, Wash. The present variety was discovered during routine orchard operation in 2003, by observation that the present variety colored earlier and to a greater extent than an adjacent 'Honeycrisp' apple tree (U.S. Plant Pat. No. 7,197), representing the parent of the present variety. The mutation resulting in the present variety (or "mutant variety") was spontaneous. The mutant variety was grafted onto then existing Sansa apple trees (U.S. Plant Pat. No. 6,519) during the 2004 growing season. This grafting took place within the same orchard. In 2006, scion wood was removed from this earlier grafted tree, and then grafted onto other Sansa apple trees (U.S. Plant Pat. No. 6,519) growing in this same orchard.

Signed and Sealed this
Twelfth Day of November, 2013

Teresa Stanek Rea

Teresa Stanek Rea
*Deputy Director of the United States Patent and Trademark Office*